United States Patent
Wittens et al.

[11] Patent Number: 5,976,077
[45] Date of Patent: Nov. 2, 1999

[54] SURGICAL ENDOSCOPIC INSTRUMENT

[75] Inventors: Cees H. A. Wittens, Rotterdam, Netherlands; Monika Loeffler, Hamburg; Michael Wiegand, Glinde, both of Germany

[73] Assignee: Olympus Winter & Ibe GmbH, Hamburg, Germany

[21] Appl. No.: 08/905,450

[22] Filed: Aug. 4, 1997

[30] Foreign Application Priority Data

Aug. 6, 1996 [DE] Germany ................. 196 31 677

[51] Int. Cl.⁶ ....................................................... A61B 1/06
[52] U.S. Cl. .................... 600/182; 600/164; 600/154; 600/107; 600/160; 385/117; 385/119
[58] Field of Search .................................. 600/104, 107, 600/130, 131, 153, 154, 138, 156, 158, 160, 164, 173, 182; 385/117, 119

[56] References Cited

U.S. PATENT DOCUMENTS

| | | |
|---|---|---|
| 4,267,828 | 5/1981 | Matsuo ........................................ 600/182 |
| 4,407,273 | 10/1983 | Ouchi ........................................ 600/182 |
| 4,607,619 | 8/1986 | Sieke et al. ............................... 600/158 |
| 5,025,778 | 6/1991 | Silverstein et al. . |
| 5,048,508 | 9/1991 | Storz ........................................ 600/154 |
| 5,313,934 | 5/1994 | Wiita et al. ............................. 600/182 |
| 5,372,582 | 12/1994 | Skrabal et al. .......................... 604/164 |
| 5,386,817 | 2/1995 | Jones ........................................ 600/158 |
| 5,495,286 | 2/1996 | Adair ........................................ 600/160 |
| 5,554,100 | 9/1996 | Leiner et al. ............................ 600/182 |
| 5,630,788 | 5/1997 | Forkner et al. ......................... 600/182 |

FOREIGN PATENT DOCUMENTS 29 26 919  1/1981  Germany .
WO 95/14425  6/1995  WIPO .

Primary Examiner—Richard J. Apley
Assistant Examiner—Ira Hatton
Attorney, Agent, or Firm—Walter C. Farley

[57] ABSTRACT

A surgical endoscopic instrument for surgery in a region directly underneath a layer of tissue covering a body cavity and traversed by the instrument which has a tubular sleeve with an operating duct and an optical system. The optical system image guide exits through a lateral outlet, the operating duct is mounted in a cross-sectional zone adjacent to the outlet and the optical system is mounted in a cross-sectional zone of the sleeve substantially opposite the outlet. The image guide of the operating duct extends laterally around the sleeve.

8 Claims, 3 Drawing Sheets

SURGICAL ENDOSCOPIC INSTRUMENT

FIELD OF THE INVENTION

The invention relates to a surgical endoscopic instrument for surgery in the region directly underneath a layer of tissue covering a body cavity, the instrument having a tubular sleeve with an operating duct designed to axially pass a surgical implement and optics comprising an image guide and aligned with the direction of viewing of its objective onto the surgical region, and a proximal end piece within which the optical system is affixed and from which issues the image guide through a lateral outlet.

BACKGROUND OF THE INVENTION

Instruments of this general type are used in surgery directly underneath a layer of tissue which, in general, is covered outside by the body skin and in a body cavity which may be natural or artificial. The main application for which the instruments of this type have been developed relates to work on the penetrating veins of the human leg. To explain the specific applications of such instrument, the surgical endoscopic treatment of penetrating veins is elucidated below.

Blood from the human leg is discharged through a parallel vein system. Deep veins carry most of the blood flow to be carried away. Surface veins that run in the vicinity of the skin only contribute 10% to the blood removal. Cross-connections are present in several places between the deep and the surface veins and are the so-called perforating or penetrating veins; they comprise inward branches along their paths.

Disorders in the surface vein system entail a number of diseases ranging from merely cosmetic varicose veins to large-scale tissue destruction. A series of techniques are available to surgically remedy these problems, wherein illustratively only the penetrating veins are ligated or the outer veins are removed in full. In each case, work is required on the penetrating veins to ligate or sever them and to seal the severed ends.

Open surgery on such work on the penetrating veins is complex and leaves scars behind. For this reason, endoscopic technology is gaining acceptance.

The known and standard instrumentation used in endoscopic work in this field, and which may be considered the precursor of the instrument of the type described herein, was described in the report, "Endoscopic Subfascial Sectioning of Incompetent Performing Veins in Treatment of Primary Varicosis", M. Jugenheimer, Th. Junginger, World J. Surgery. 16, pp 971–975, 1992. This instrument is composed of a proximal, open sleeve with a grip, optics with grip and with a surgical implement inserted into the sleeve. Surgery takes place in the space between the muscle and the fascia enclosing the muscle, this space being easily enlarged into a surgical space by lifting the fascia from the muscle.

This instrumentation entails drawbacks because several elements must be held and actuated, requiring more than two hands. Moreover, the sleeve is open and as a result gas evacuation, for instance to remove smoke and vapor during electro-surgery or gas to allow insufflation to widen the surgical space, are precluded.

An instrument of this species is described in the document WO 95/14425. This instrument comprises a sleeve with integrated optics. Both parts may be thus operated with one hand. The other hand remains free to operate the surgical implement, such as scissors, a knife or a high-frequency (hf) cutting electrode to sever the penetrating vein, or a coagulating implement or a clip applicator to seal the penetrating vein, and the like. Improved sealing is attained by the integrated design. For instance, a rubber lip sealing the surgical implement may be mounted at the proximal end of the operating duct. Insufflation and evacuation are improved thereby.

In this design the optics is mounted in the cross-sectional zone of the sleeve near the outlets, whereas the operating duct is mounted opposite the outlets. The design is simplified because the operating duct is not in the way of guiding the image and light guides from the optics into the outlets.

It is standard procedure to insert such an instrument through a pierced duct underneath the skin and the muscle fascia into the space between the muscle and the fascia and to advance the instrument therein up to a penetrating vein to be operated on and, possibly, thereafter to be advanced farther to another penetrating vein to be operated on. In the process and by its nature the instrument will rest with its outer proximal end projecting from the skin directly against the leg. For reasons of space and handling, the outlets must be directed away from the leg.

Accordingly, the instrument inner duct of known design points toward the inside of the leg whereas the optics points toward the outside of the leg, that is, toward the fascia. As a result, however, an implement, such as a clip applicator, inserted through the operating duct into the space between the fascia and the muscle where the penetrating vein will be operated on, lies against the muscle. Only at this location is it possible to conveniently operate on the penetrating vein.

On the other hand, operating is disadvantageous at this site, near the muscle, of the penetrating vein, because this vein has branches in the region between fascia and muscle. Supply to the penetrating vein must take place outside those branches, that is as far as possible outside at the fascia.

But in the known instrument, which is located toward the muscle, surgery on the fascia-near zone of a penetrating vein is possible only at great pains. High leverage forces must be applied to the instrument, entailing difficulty and possibly unwanted injuries.

German patent document 29 26 919 C2 discloses an endoscopic instrument wherein the optics, the image guide and a separately emplaced light guide are mounted in the tubular sleeve on one side of its cross-section, whereas the operating duct is located on the other side of the cross-section. However, differing from the design of patent document WO 95/14425, the outlet of the light guide is on the other side of the tubular sleeve, where the operating duct is located. In relation to the tubular sleeve the two outlets therefore are diametrically opposite. Obviously such an instrument is presently inapplicable because the light guide outlet would be in the immediate vicinity of the body on account of the required angular position with the image guide outlet away from the body.

SUMMARY OF THE INVENTION

An object of the invention is to provide an instrument that facilitates surgery within an artificially created body cavity underneath a tissue layer and in the zone directly underneath said tissue layer.

In the instrument of the invention, the positions of an optical system and the operating duct in the sleeve are the reverse, relative to the outlet positions, of what they are in the known instrument of this type. In the above described surgery position of the instrument, wherein the outlets point away from the body, the instrument inserted through the operating duct already by design will be externally close to the tissue layer in that zone where, for instance in special applications, surgery on the penetrating vein will be most advantageous. Cumbersome and patient-traumatizing attempts to arrive by shaft leverage into the range of the penetrating vein thus can be eliminated.

By providing a disconnectable coupling between the sleeve and end piece, cleaning of the instrument can be improved and it is possible to use sleeves of different cross-sections depending on need.

As regards the instrument of the invention, the optical system as well as the operating duct are present in an inside sleeve tightly surrounded by the sleeve to form a separate suction duct. As a result the cross-section of the operating duct is limited and the complex design involves several tubes.

In this light it is advantageous for the optical system to be cantilevered to the sleeve. Therein the operating duct has maximum cross-section which is restricted only as necessitated by the optical system cross-section.

Adjustment problems arise with an optical system cantilevered inside the sleeve as described. Slight adjustment errors during assembly or in the disconnect coupling connecting a coupling shaft as well as bending the optical system when being improperly handled can entail erroneous positioning of the objective over the length of the optical system and hence shifting the field of view. For that purpose, a ramp is provided in a distal end zone of the sleeve generally opposite the outlet and has a guide groove rising in the distal direction to receive the optical system. When applying the sleeve, the distal optical system end slides into the guide groove and, while the optical system is being slightly bent elastically, it will be moved into an accurately defined position. Moreover, the slight, distal obliqueness of the optical system relative to the operating duct results in alignment in the direction of the surgery zone located distally in front of the operating duct. Therefore a somewhat smaller field of view of the objective may be selected.

Providing an outlet for a suction hookup in the proximal end zone of the sleeve is advantageous. Such a suction hookup may be used in known manner to evacuate vapors arising in hf-cutting and also for insufflation to enlarge the surgery space.

It is also advantageous to mount all outlets in the same circumferential angular position. Mounting all outlets (for image guide, light guide, suction hookup, etc.) at the same angular position allows arranging them compactly and these outlets moreover may be designed or used as a grip, and all outlets are placed directly against the body in a position allowing advantageous use of the instrument.

The optical system can comprise an outer tube and an inner tube with the image guide mounted in the inner tube and the light guide in the gap between the tubes. The optical system may be mounted as a cantilever over a substantial length and as a result it is very stable. The fiber bundle conventionally used as a light guide can be mounted optically separated from the image guide which may be in the form of a bar lens optical system or as image transmitting fiber optics.

It is also advantageous to provide two axially sequential chambers in the end piece running laterally around the operating duct with the image-guide outlet issuing into the proximal light-guide chamber and the light-guide outlet issuing into the distal light-guide chamber and with the inner tube issuing into the image-guide chamber and the outer tube issuing into the light-guide chamber. The chambers allow excellent omnidirectional sealing of image guide and light guide in the critical region between the proximal optical system end and the outlets. In particular, there also is good sealing between image guide and light guide whereby moisture penetrating in the distally open fiber bundle conventionally used as light guide cannot penetrate the image guide which has humidity-sensitive lens surfaces. The chambers moreover offer good mechanical protection to the image guide and the light guide against damage, for instance, from implements inserted through the operating duct.

BRIEF DESCRIPTION OF THE DRAWINGS

The invention is schematically and illustratively shown in the drawings, wherein.

DESCRIPTION OF THE PREFERRED EMBODIMENTS

Figure 1:
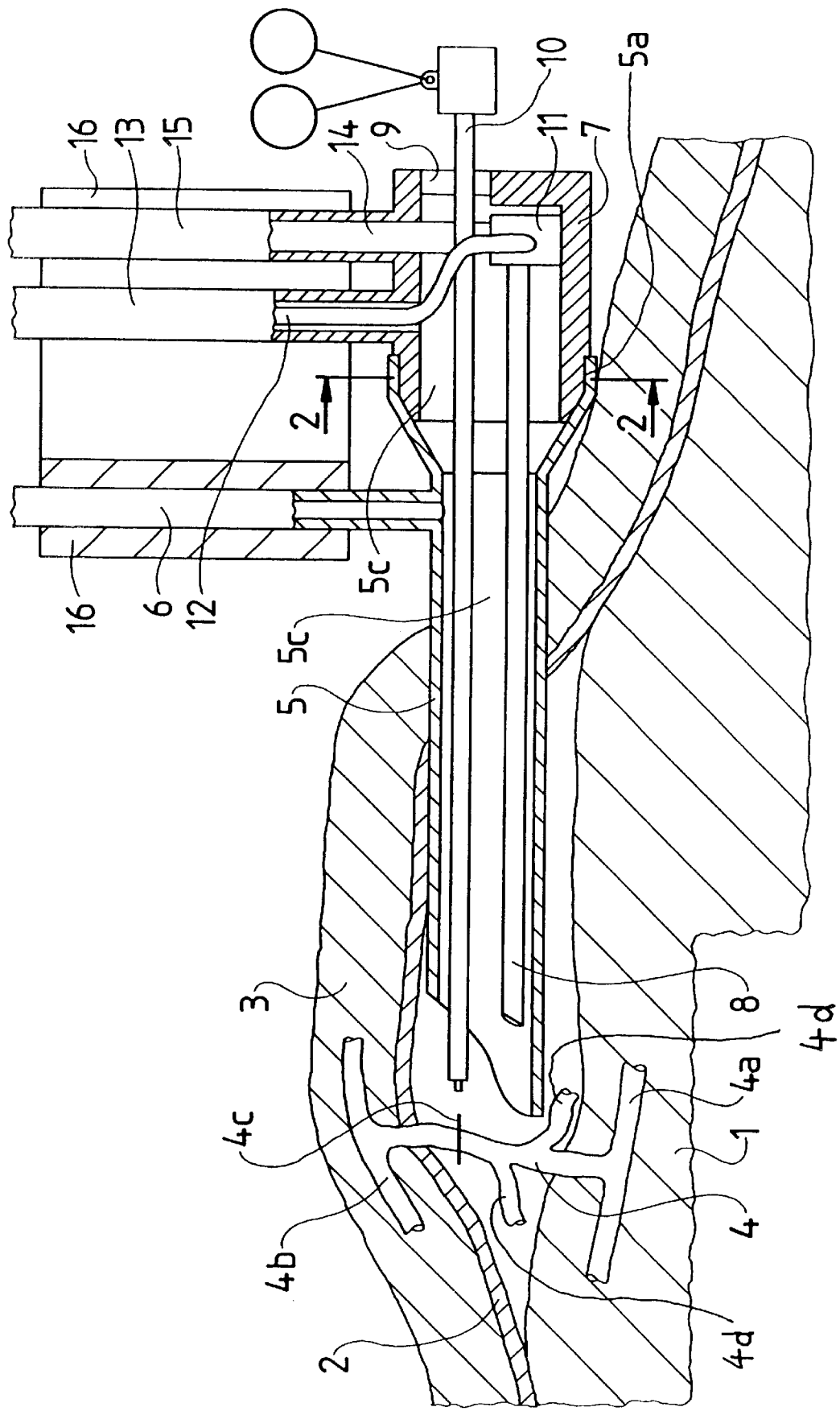
FIG. 1 is a longitudinal section of a first embodiment of an instrument of the invention in the operating position at the site of surgery.

The sectional view of FIG. 1 shows a patient's calf muscle 1, with the fascia 2 being opposite, and the externally covering skin tissue 3.

A penetrating vein 4 to be fitted with a clip 4c runs between an outer vein 4b and an inner vein 4a. The penetrating vein 4 comprises branches 4d closely below the fascia 2. Moreover, clip 4c should be located outside the branches 4d, that is, as close as possible to fascia 2.

For that purpose, the instrument is inserted by means of its tubular sleeve 5 into a pierced duct extending through the patient's skin tissue 3 and fascia 2 into the space between the surface of muscle 1 and fascia 2 and is advanced into the zone in front of penetrating vein 4. Sleeve 5 has a relatively large diameter at its proximal side where it passes through the skin tissue so that it is able to seal the pierced duct well. The diameter may be tapered in the distal end zone even though a large diameter would be advantageous here to enlarge the space between the muscle 1 and the facia 2. However, as shown in FIG. 1, such enlargement also may be implemented by insufflation of compressed inert gas.

For that purpose an outlet 6 to a suction hookup is present at the proximal end of shaft 5 to allow evacuation of hf vapors when operating on the penetrating vein and also permitting insufflation.

Sleeve 5 is connected by a schematically shown disconnect coupling 5a which is locked by means, not shown, to an end piece 7. Sleeve 5 and the end piece enclose an operating duct 5c running through the entire instrument and a cantilevered bar-optics 8 mounted by its proximal end in the end piece 7.

Operating duct 5c is accessible from the proximal end of end piece 7 by means of an aperture 9 which, where called for, may be closed by a rubber membrane to implement gas sealing while allowing passing in sealing manner a surgical implement 10.

The shown surgical implement 10 in this embodiment is a clip applicator actuated by scissor grips and used for setting clip 4c. The objective at the distal end of optical system 8 is slightly oblique to allow observing the surgical region at clip 4c.

Optical system 8 is affixed proximally in end piece 7 to an end part 11 from where a light guide 12 in the conventional form of a fiber-optics bundle runs to an outlet 13 laterally issuing from the end piece 7. An image guide 14 runs to an outlet 15. The image guide may be in the form of an image-guide fiber-optics bundle or it may be a lens optical system illustratively composed of bar lenses, deflection prisms and the like.

As shown by the Figures, the optical system is positioned in sleeve 5 opposite the positions of outlets 13 and 15. This feature offers the advantage that operating duct 5c abuts outlets 13 and 15. As shown by FIG. 1, outside the body, end piece 7 rests very close to the skin of the patient. Therefore, outlets 13 and 15 and also outlet 6 for the suction connectors can be directed only away from the patient. A grip 16 enclosing outlets 6, 13 and 15 may be provided for improved handling.

In the constrained angular position of the instrument shown in FIG. 1, the outward operating duct 5c points to fascia 2, or to the skin tissue 3, whereas the inward optical system 8 points to muscle 1. As shown by FIG. 1, clip 4c may be affixed to the outer end of the penetrating vein 4 while this process is observed through optical system 8 of which image guide 14 and light guide 12 are connected (in a manner which is not shown) outside the instrument to an ocular or a video camera or a light source.

Figure 4:
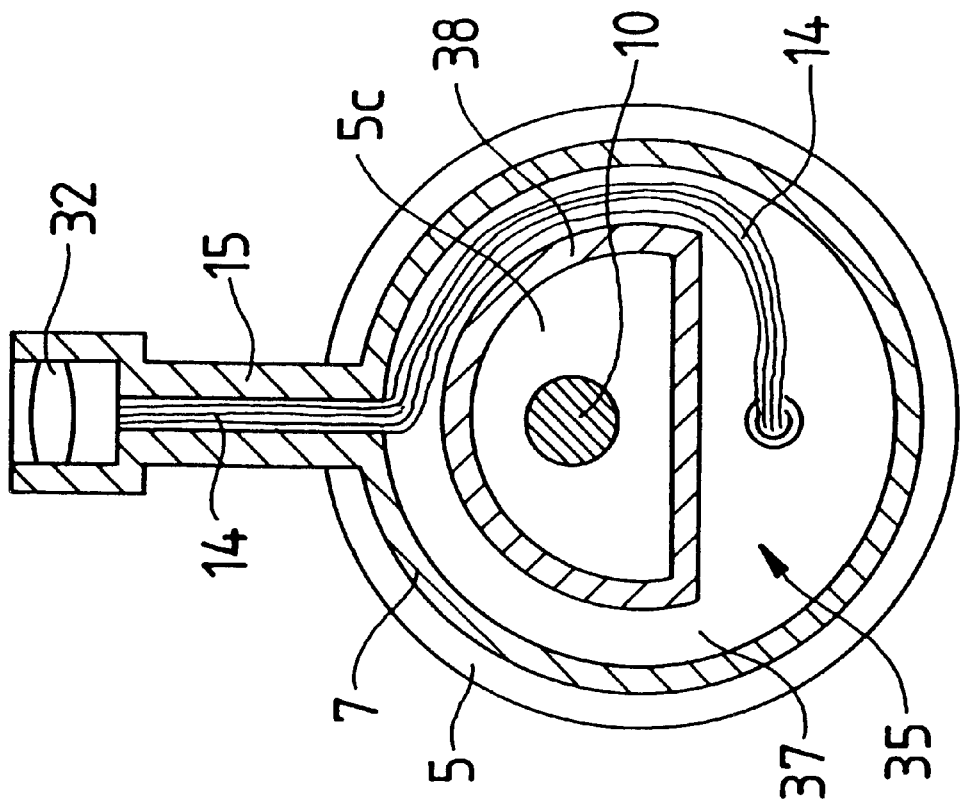
FIG. 4 is a section along line 4—4 of FIG. 3.
Figure 2:
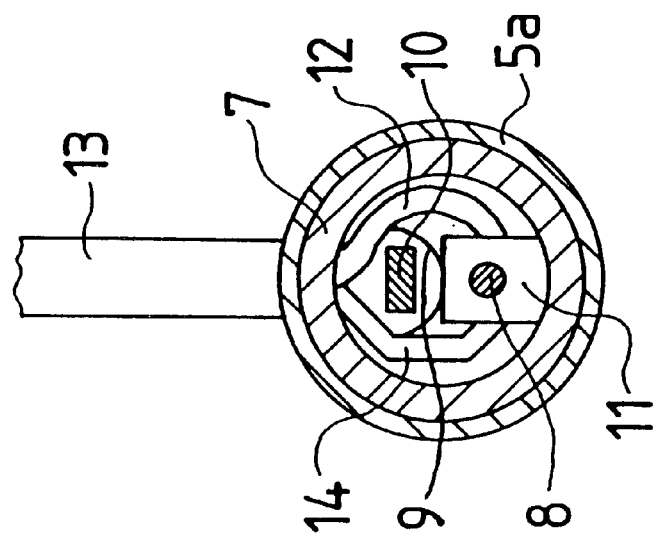
FIG. 2 is a section along line 2—2 of FIG. 1.
Figure 3:
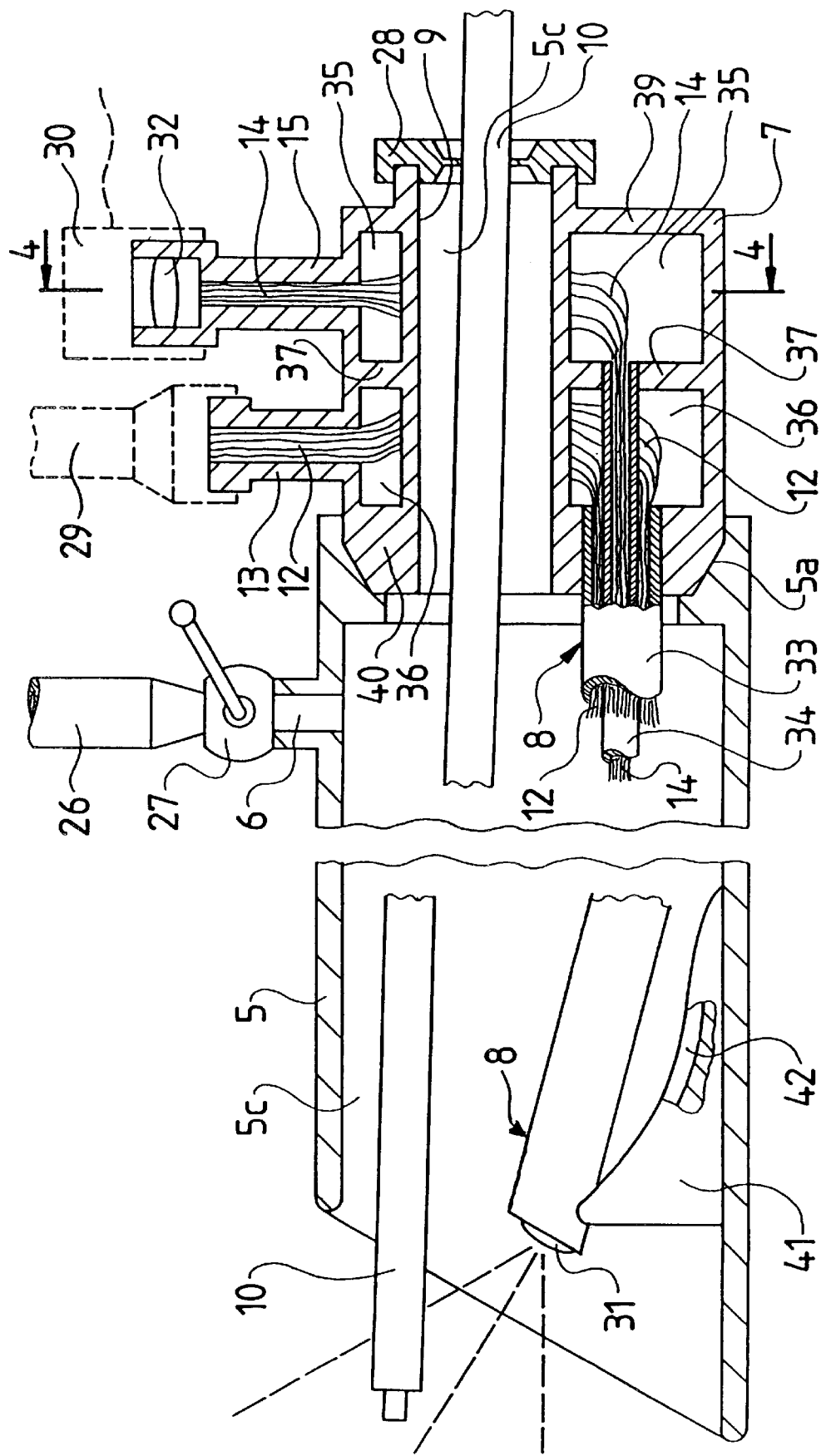
FIG. 3 is an enlarged section similar to FIG. 1 of a further embodiment of an instrument in accordance with the invention.

FIGS. 3 and 4 show a further embodiment, retaining as much as possible the reference numerals used in FIGS. 1 and 2.

Sleeve 5 of this instrument again is coupled by a disconnect coupling 5a with locking means (not shown) to end piece 7. It comprises an outlet 6 for the suction connection to the hookup hose 26 and valve 27.

The operating duct 5c is proximally accessible through aperture 9 fitted with a membrane 28 hermetically sealing the surgical implement 10 while enclosing operating duct 5c.

A light-guide cable 29, shown in dashed lines, can be connected to the stub-shaped outlet 13 for light-guide 12 in the form of a fiber-optics bundle and leads to a cold-light source, not shown. A video camera 30, shown in dashed lines, can be connected to outlet 15, also in the form of a stub, of image guide 14, or it may be replaced by an ocular for eye observation.

In the embodiment of FIG. 3, the image guide 14 is designed as an image-guide bundle. It guides the image from the objective lens 31 at the distal end of optical system 8 to an ocular lens 32 at the outer end of the outlet 15. These lenses, or, where called for, additional windows, seal the ends of image guide 14 against penetrating liquid that would fog the lens surfaces and thus blur the image.

Optical system 8 comprises an outer tube 33 and an inner tube 34. The image guide 14 is placed inside the inner tube 34 and the light guide 12 is placed in the gap between the tubes 33 and 34.

An image-guide chamber 35 and a light-guide chamber 36 are in end piece 7. Said chambers run annularly, as shown at 35 in FIG. 4, relative to operating duct 5c bounded by a sheath tube 38. They are mutually partitioned by a wall 37. Image guide chamber 35 is closed proximally by an end wall 39 and light guide chamber 36 is closed distally by an end wall 40.

Outer tube 33 of optical system 8 rests in distal end wall 40 and, as a result, its inner space issues into light guide chamber 36. Light guide 12 passes through chamber 36 and runs around operating duct 5c as far as its outlet 13.

Inner tube 34 of optical system 8 runs through light guide chamber 36 and terminates in wall 37 partitioning the two chambers, that is, it issues into image guide chamber 35. The image guide passes through chamber 35 and around operating duct 5c as far as its outlet 15 as shown in FIG. 4.

In this manner it is possible to mutually bound image guide 14 and light guide 12 over their entirely lengths in a complete manner so that water entering the terminally open fiber bundle of light guide 12 cannot reach image guide 14.

FIG. 3 shows that a ramp 41 is mounted on the inside wall of the distal end zone of sleeve 5 and is offset by 180° in its circumferential angular position relative to the positions of outlets 13 and 15. Ramp 41 comprises a guide groove 42 rising from its proximal end to its distal end and located with its distal end in the middle cross-sectional zone of sleeve 5.

When the disconnect coupling 5a is open and sleeve 5 is removed, optical system 8 of the embodiment of FIG. 3 is aligned with the instrument axis as shown in FIG. 1. If sleeve 5 is slipped over optical system 8 as far as end piece 7 in order to be locked with it, then the distal end of optical system 8 slides in guide groove 42 upward as far as into the end position shown in FIG. 3. In the process, optical system 8 will be slightly bent and now is stressed against the distal end of guide groove 42 which retains it securely in the position shown, regardless of any adjustment errors. Accordingly, optical system 8 always will be in its appropriate position following assembly of sleeve 5 wherein objective 31 will cover the surgical region.

What is claimed is:

1. A surgical endoscopic instrument for performing surgery in a surgical region directly underneath a layer of tissue (2, 3) outwardly covering a body cavity and penetrated by the instrument, comprising a tubular sleeve (5) having a proximal end piece (7) and an operating duct (5c) axially extending through said sleeve and end piece, said end piece supporting and retaining said sleeve (5) and having an outlet (15) extending in one direction from a side of said end piece;

an optical system (8) mounted in said end piece and axially extending through said duct in a distal direction and, in cross-section, at a side opposite said outlet, said optical system including an objective (31) directed to view said surgical region; and an image guide (14) mounted on said outlet and connected to said optical system, said image guide (14) having a portion extending through said end piece (7) and laterally passing around the operating duct (5c) from the proximal end of said optical system (8) to said outlet (15).

2. An instrument according to claim 1 and including a disconnect coupling (5a) joining said sleeve (5) to said end piece (7).

3. An instrument according to claim 1 wherein said optical system (8) is mounted as a cantilever in said sleeve (5), said operating duct (5c) comprising the remaining interior of said sleeve.

4. An instrument according to claim 3 and including a ramp (41) in an inside distal end zone of said sleeve (5) on a side generally opposite said outlet (15), said ramp including a guide groove (42) inclined radially inwardly and distally from an inside wall of said sleeve to a middle cross-sectional zone of said sleeve (5) receiving a distal portion of said optical system (8).

5. An instrument according to claim 1 and further including an outlet (6) for a suction hookup in a proximal end zone of said sleeve (5).

6. An instrument according to claim 1 wherein said end piece supports a plurality of outlets and wherein all said outlets (6, 13, 15) extend in the same circumferential angular position.

7. An instrument according to claim 1 wherein said optical system (8) comprises an outer tube (33) and an inner tube (34), wherein a portion of said image guide (14) is mounted in said inner tube (34), and wherein said light guide (12) occupies a gap between said tubes (33, 34).

8. An instrument according to claim 7 wherein said end piece comprises two axially sequential chambers (35, 36) extending around said operating duct (5c) including a proximal image-guide chamber and a distal light-guide chamber, said image-guide outlet (15) entering said proximal image-guide chamber (35) and a light-guide outlet (13) entering said distal light-guide chambers (36), and wherein said inner tube (34) enters into said image-guide chamber (35) and said outer tube (33) enters into said light-guide chamber (36).

* * * * *